United States Patent [19]
Imonti

[11] Patent Number: 4,870,977
[45] Date of Patent: * Oct. 3, 1989

[54] SURGICAL PROTECTOR FOR RAISED WOUNDS

[75] Inventor: Maurice M. Imonti, Dana Point, Calif.

[73] Assignee: CooperVision, Inc., Palo Alto, Calif.

[*] Notice: The portion of the term of this patent subsequent to Jul. 5, 2005 has been disclaimed.

[21] Appl. No.: 73,081

[22] Filed: Jul. 14, 1987

Related U.S. Application Data

[63] Continuation-in-part of Ser. No. 28,673, Mar. 20, 1987, Pat. No. 4,754,750.

[51] Int. Cl.⁴ .................. A61J 13/00; A61F 13/00; A61M 27/00
[52] U.S. Cl. .................. 128/890; 128/155; 604/346; 623/7; 450/81
[58] Field of Search ........... 128/150, 155, 156, 132 R, 128/360, 890; 215/11.1, 11.3, 11.4; 206/222; 604/346, 892, 896, 897; 623/7, 8; 450/39, 40, 57, 81

[56] References Cited

U.S. PATENT DOCUMENTS

| | | | |
|---|---|---|---|
| 1,967,923 | 7/1934 | Connolly | 128/156 |
| 2,221,758 | 11/1940 | Elmquist | 128/132 R |
| 2,448,938 | 9/1948 | Wayne | 604/346 |
| 2,495,307 | 1/1950 | Abramson | 128/150 |
| 2,604,092 | 7/1952 | Brown et al. | 604/346 |
| 3,677,225 | 7/1972 | Czirely | 128/132 R |
| 4,333,471 | 6/1982 | Nakai | 128/150 |
| 4,754,750 | 7/1988 | Imonti | 128/155 |

FOREIGN PATENT DOCUMENTS

| | | | |
|---|---|---|---|
| 0007772 | 2/1893 | United Kingdom | 128/150 |
| 0836238 | 4/1952 | Fed. Rep. of Germany | 128/150 |
| 2464064 | 4/1981 | France | 128/156 |
| 2577798 | 8/1986 | France | 128/156 |
| 0273631 | 4/1930 | Italy | 128/150 |

Primary Examiner—Richard J. Apley
Assistant Examiner—Paul Prebilic
Attorney, Agent, or Firm—Vorys, Sater, Seymour and Pease

[57] ABSTRACT

An areola/nipple surfical wound protector including a sterile pad having an upper surface, a lower non-stick surface and a centrally-located pad opening extending through it. A transparent cone-shaped nipple protector member having an outwardly-disposed flange at its base portion is secured via the flange to generally the upper pad surface and over the pad opening. The nipple protector member has an opening in its base portion, a dome with holes therethrough at its radially opposite end and an interior configured to receive the patient's nipple up through the opening and into the protector member. Spaced adhesive tape strips extend radially out from the pad for securing the pad and protector member to the patient's breast and over her nipple. Alternatively, the dome can be configured to be flatter on its upper surface and have a large medication opening through the center thereof and a surrounding rasied annular rim having a plurality of suture holes therethrough. The reconstructed nipple can then be sutured through the suture holes and relative to the protector member so that it stands up and can heal without slumping down or over. With the subject wound protector in place medications can be applied to the reconstructed nipple through this medication opening.

36 Claims, 2 Drawing Sheets

SURGICAL PROTECTOR FOR RAISED WOUNDS

BACKGROUND OF THE INVENTION

This is a continuation-in-part of co-pending application Ser. No. 028,673, filed Mar. 20, 1987 now U.S. Pat. No. 4,754,750.

The present invention relates to bandages and more particularly to surgical bandages for the areola and nipple area of a woman's breast following a radical mastectomy.

Following a radical mastectomy it is necessary to rebuild the patient's breast, and silicone implants are used to give the new breast the needed mass. Tissue is taken from the vaginal area or ear lobe to construct the nipple and then the surrounding area is tattooed to match the coloring of the woman's other breast. In the past to then protect the surgically-created nipple and surrounding areola several loose sterile pads were taped in place, and the end of a syringe was cut off and positioned over the new nipple to cover it and then taped into place with the loose sterile pads.

This bandage construction requires a great deal of manipulation thereof and thus has proven to not b as sterile as desired, and often this bandage would not sufficiently protect the new tissue from the unsanitary environment especially when it was not carefully applied. Also the manipulation is uncomfortable to the patient, and the patient could not herself as a practical matter make and change her own bandage. It also often would not be form fitting and so discomfort would result from excessive contact with the newly-formed tissues. Further, the involved manipulating procedure of constructing and applying this bandage and its "jury-rigged" appearance have often been discomforting to women who have undergone the emotional trauma of a radical mastectomy. This bulky bandage may also not allow the overlying clothing to hang smoothly over the reconstructed breast. The bandage also does not provide any outward support for the nipple so that during the healing process the nipple would tend to fall to one side or the other against the encircling cut syringe body or slump down within the syringe body, and then heal in that slanted or slumped position. Further, if it was later desired to apply any type of medication to the reconstructed nipple, the bandage would first have to be removed and then subsequently either that bandage or preferably a new bandage applied which is a very discomforting procedure for the woman.

OBJECTS AND SUMMARY OF THE INVENTION

Accordingly, it is a principal object of the present invention to provide an improved bandage design for the nipple and areola area of a breast which has undergone a radical mastectomy.

Another object of the present invention is to provide a novel wound protector for the areola and nipple area which protector is ready for use and can be quickly and easily applied by the woman who has undergone a radical mastectomy.

A further object of the present invention is to provide an improved bandage for the areola and nipple area which bandage is carefully configured so as to minimize contact with the reconstructed tissue of that area and to thereby minimize any resulting discomfort.

A still further object is to provide a novel bandage designed for a reconstructed areola and nipple area which provides aeration of the nipple to promote healing thereof while minimizing communication with the unsanitary environment.

Another object is to provide an improved surgical wound protector bandage construction which has the appearance of professional and sound manufacture so the patient will be more confident and at ease with it.

A further object is to provide a novel structure for holding a reconstructed nipple in position so that it may properly heal.

A still further object is to provide an improved protector bandage for a nipple which allows for administration of medications to the nipple with the protector bandage in place on the breast.

Another object is to provide an improved nipple protector design having smooth surfaces so that the woman's clothing will not cling to it.

The subject surgical wound protector invention is designed for protecting raised wounds, such as reconstructed areola/nipple areas of a woman's breast, and is directed to achieving the foregoing objects and overcoming problems proposed in the art. A transparent cone-shaped protector member of the wound protector is secured at its radical base flange to a sterile pad. An adhesive tape system secures the pad and protector over the raised wound so that the wound extends up through an opening in the pad into the protector member. A preferred design of the protector member has a generally flat upper surface. A large medication opening passes through the center of that surface is surrounded by a raised annular rim having a plurality of spaced suture holes through it. The raised wound, such as a reconstructed nipple, in the protector member can then be sutured through the suture holes so that it can stand up in the protector member without slumping down or over to promote proper healing thereof. Also medications can be applied to the raised wound through the medication opening without the inconvenience and risks associated with removing the wound protector once in place from over the wound.

Other objects and advantages of the present invention will become more apparent to those persons having ordinary skill in the art to which the present invention pertains from the following description taken in conjunction with the accompanying drawings.

DETAILED DESCRIPTION OF THE PREFERRED EMBODIMENTS

Figure 1:
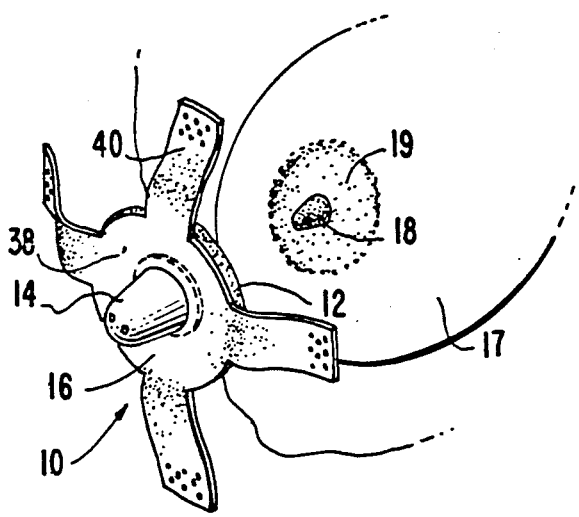
FIG. 1 is a perspective view of a first surgical wound protector of the present invention showing the application thereof to the breast of a woman who has undergone a radical mastectomy.

Referring to FIG. 1 a first surgical wound protector of the present invention is illustrated generally at 10 and is formed of three basic components, namely, a generally circular sterile pad 12, a cap or nipple protector member centrally positioned on the pad and shown generally at 14, and a tape securing construction 16 designed to both hold protector member 14 to sterile pad 12 and also to hold the sterile pad and protector member to the woman's breast 17 when positioned over her nipple 18 and areola 19.

Pad 12 is a sterile pad of about 3/16 or ⅛ inch thickness and having a 2½ inch diameter as shown at 20. It has a non-sticking lower surface 21 to be positioned against the patient's breast 17, an upper surface 22, and a ¾ inch diameter hole 24 centrally positioned and passing therethrough.

Figure 4:
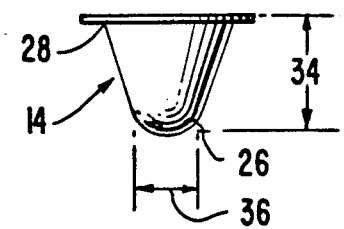
FIG. 4 is a side elevational view of the nipple protector member of the surgical wound protector of FIG. 1 shown in isolation.
Figure 5:
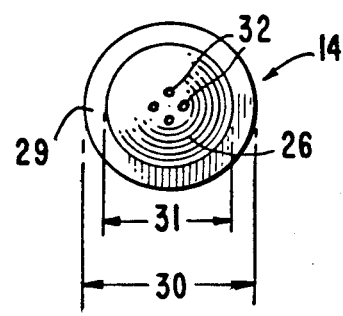
FIG. 5 is a top plan view of the nipple protector member of FIG. 4.
Figure 7:
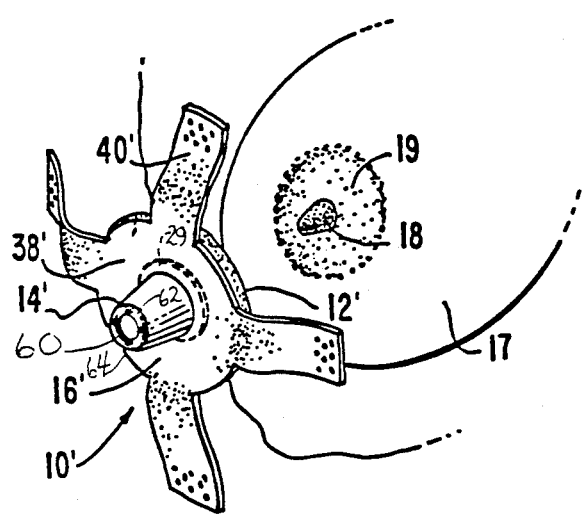
FIG. 7 is a perspective view of a second surgical wound protector of the present invention showing the application thereof to the breast of a woman who has undergone a radical mastectomy.
Figure 8:
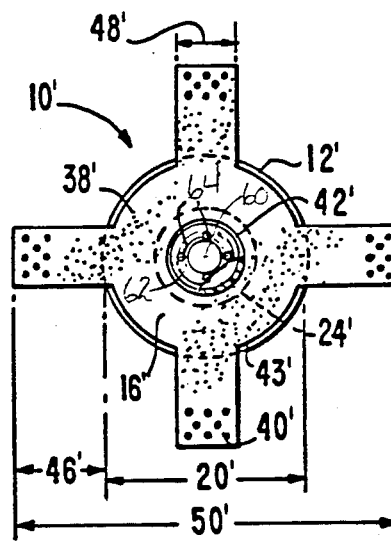
FIG. 8 is a partially fragmentary top plan view of the wound protector of FIG. 7 shown before application thereof.
Figure 9:
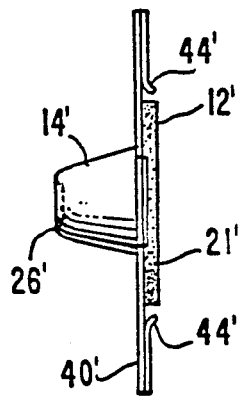
FIG. 9 is a side elevational view of the wound protector of FIG. 7.

Protector member 14 is preferably cone-shaped and has a dome-shaped top 26 and a base portion 28. An annular flange 29 extends radially out from base portion 28 and has an outer diameter of 1.25 inches as shown at 30 in FIG. 5. The diameter of base portion 28 is 1.00 inch as depicted in the drawings by numeral 31. At the tip of dome-shaped top 26 are four symmetrically-spaced holes 32 each having a diameter of about 0.062 inches and providing aeration of the enclosed healing nipple 18 while protecting it from the unsanitary environment. Nipple protector member 14 is formed of a tissue-compatible plastic material of about 0.20 inch thickness. The plastic material is preferably clear so that the healing condition of the nipple 18 can be easily be viewed without removing wound protector 10. Protector member has a height of 0.88 or 0.75 inch as shown at 34 in FIG. 4 and a diameter of the dome-shaped top as best shown in FIG. 4 at 36 of 0.62 inch. As can be appreciated, the interior of nipple protector member 14 is configured to receive the nipple 18 therein but is slightly larger so as to minimize the contact with the nipple once in position therein. Centrally located hole 24 in the pad is slightly smaller than the base portion hole 37 in the protector member and preferably is 0.750 inch in diameter. Thus, as can be appreciated from FIG. 6, the delicate nipple tissue will touch the softer pad 12 which will soften any contact with the harder plastic nipple protector member 14.

Figure 2:
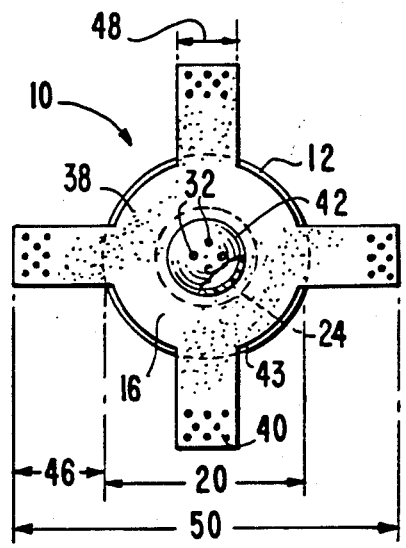
FIG. 2 is a partially fragmentary top plan view of the wound protector of FIG. 1 shown before application to the woman's breast.
Figure 3:
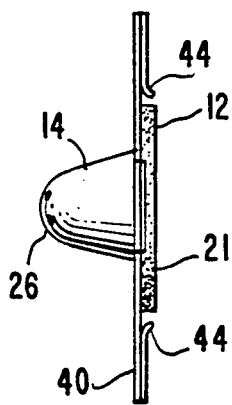
FIG. 3 is a side elevational view of the wound protector of FIG. 1.
Figure 6:
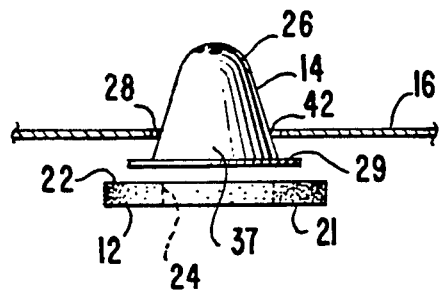
FIG. 6 is a side elevational view showing in schematic form the securing of the protector member of FIG. 4 to the underlying pad of the wound protector of FIG. 1.

Tape securing construction 16 is provided for both securing the nipple protector member 14 to pad 12 as well as for securing pad 12 and protector member 14 over the nipple 18 and to the patient's breast. It comprises a continuous piece of tape having an inner circular portion 38 and four perforated tape strips 40 extending radially out from the circular portion. Inner circular portion 38 has a 0.875 inch diameter hole 42 in the center which then fits over protector member 14 as best illustrated in FIG. 6 engaging the upper surface of annular flange 29 to thereby hold the nipple protector member 14 securely on upper surface 21 of the pad. The inner circular portion 38 of the tape is slightly smaller than pad as best shown in FIG. 2, thereby defining a rim 43 of gauze pad so that the edges of circular portion 38 do not rub against the breast. Tape securing construction 16 is formed of a breathable FDA approved pressure sensitive tape, preferably perforated, and a protective paper tape 44 as shown in FIG. 3 removable before application is provided on the back surface of each one of the tape strips 40. As best illustrated in FIG. 2, tape strips 40 are positioned ninety degrees relative to each other and are 1.00 inch long typically as shown at 46 and 0.75 inch wide typically as shown at 48 and thus will extend 4.00 or 4.50 inches typically from the tip of or outer end of one strip to the outer end of the opposite diametrical strip as depicted by dimension 50. The tape strips 40 may also be sized so that two of them are longer than the other two, such as two each having lengths 46 of 1.00 inch and the other two having lengths of 2.00 inches.

A second surgical wound protector of the present invention is illustrated in FIGS. 7-11 generally at 10'. As will be appreciated there are many similarities between wound protector 10' and previously-described wound protector 10 and so similar parts are designated by the same number but with a prime designation thereafter and reference is made to the prior corresponding description for each of these similar parts.

Figure 10:
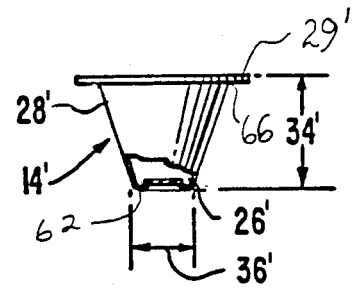
FIG. 10 is a side elevational view of the nipple protector member of the surgical wound protector of FIG. 7 shown in isolation.
Figure 12:
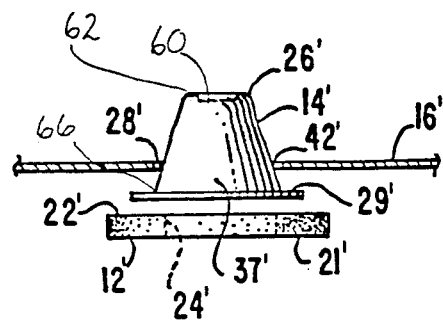
FIG. 12 is a side elevational view showing in schematic form the securing of the nipple protector member of FIG. 10 to the underlying pad of the wound protector of FIG. 7.
Figure 11:
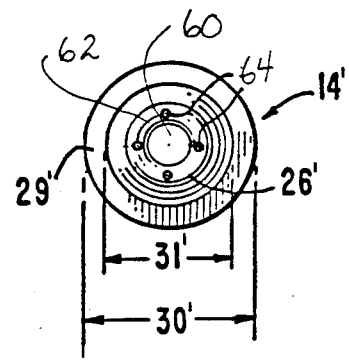
FIG. 11 is a top plan view of the nipple protector member of FIG. 10.

Referring to FIGS. 7-11 it is seen that the top 26' of protector member 14' is generally flatter than dome top 26, and has a centrally disposed medication opening 60 passing therethrough and through which medications such as softening salves can be applied to nipple 18 with wound protector 10' in place, i.e. without removing it from the patient's breast 17. An annular rim 62 is provided at the edge of the top and surrounding and defining the outer edge of medication opening 60. This rim construction adds rigidity to the nipple guard or protector member and provides surface so that clothing will not cling. A plurality of spaced suture holes 64 pass through the top surface of rim 62. Suture holes 64 preferably consist of four holes each having 0.040 inch diameters and spaced ninety degrees relative to each other on a 0.56 inch diameter circle. The outer diameter 36' of the rim 62 is preferably 0.62 inch, as best shown in FIG. 10, the rim in cross section defines a small semicircle of 0.040 inch radius, and the inner diameter of rim 62 is then 0.38 inch. The height 34' of protector member 14 is 0.75 inch and the diameter 31' is 0.88 inch. The base portion 28' connects to annular flange 29' at outside annular connection surface 66 with a rounded joint having a maximum radius of 0.015 inch.

The newly-constructed nipple often tends to lean or sag during the healing process and so the present invention provides for circumferentially and radially spaced suture holes 64 in protector member 14'. After the wound protector 10' has been positioned over nipple 18 and secured to breast 17 with tape strips 40', the nipple 18 is sutured to stand straight in protector member 14' and spaced from the side walls thereof to heal with the proper shape and orientation. Using a half-moon shaped needle (not shown) and numbers four or ten (nylon)

thread (also not shown) the nipple 18 is sewn through suture holes 64 to stand in position. The thread can be tied off either outside of rim 62 or inside as through medication opening 60. If medications need to be applied later to the nipple 18 this can be done through medication opening 60 without removing the sutures.

The surgical wound protector 10 or 10' of the present invention can be individually packaged for distribution in sterile packages (not shown) which can easily be torn open by the user. As can be appreciated, the subject surgical wound protectors are convenient to apply to the breast by the doctor or other medical personnel as well as by the patient herself. They are constructed so as to minimize contact with the delicate nipple and areola area and also constructed so as to promote healing of this area. Further, the subject surgical wound protectors present a professionally sound appearance so as to give the patient more confidence in her use thereof. Although the subject surgical wound protector invention has been pictured and described in its use as a protector for a reconstructed and healing areola and nipple of a recovering radical mastectomy patient, other wound protecting uses are within the scope of the present invention. These uses include but are not limited to supports for trachea tubes and drainage tubes, and also protectors for raised boils and umbilical cords.

From the foregoing detailed description, it will be evident that there are a number of changes, adaptations, and modifications of the present invention, including changes to the various dimensions and materials stated herein, which come within the province of those skilled in the art. However, it is intended that all such variations not departing from the spirit of the invention be considered as within the scope thereof as limited solely by the claims appended hereto.

What is claimed is:

1. A method of caring for the areola and nipple area of a patient's breast following a radical mastectomy comprising:
    providing a wound protector bandage comprising a protector cap having a base opening and configured to receive the patient's reconstructed nipple thereinto up through said base opening, a pad attached to said protector cap at the base thereof, and said protector cap defining a plurality of suture holes therethrough,
    positioning said wound protector bandage over the patient's reconstructed nipple with said nipple being disposed in said cap,
    attaching the pad of said positioned wound protector bandage to the patient's breast, and
    suturing through said suture holes said nipple to position it relative to said cap.

2. The method of claim 1 wherein said suturing includes suturing said nipple in position up from the base portion of said cap and centrally in said cap so as to be spaced from all of the side walls thereof.

3. The method of claim 1 further comprising said protector cap having a medication opening generally larger than said suture holes passing therethrough, and with said protector bandage attached to the patient's breast, applying medication to the nipple through said medication opening.

4. The method of claim 1 wherein said suturing step includes tieing off the suture threads through the medication opening.

5. The method of claim 1 wherein said applying step is after said suturing step.

6. A method of treating a reconstructed nipple and surrounding areola area of a patient's breast comprising the steps of:
    providing a wound protector bandage including a protector cap having a base opening and configured to receive the reconstructed nipple thereinto up through the base opening, a pad attached to the protector cap at the base thereof, and said protector cap having a medication opening therethrough,
    positioning the wound protector bandage over the reconstructed nipple with the nipple disposed in the protector cap,
    attaching the pad of the positioned wound protector bandage to the patient's breast, and
    thereafter and with the protector bandage still attached to the patient's breast, applying medication to the reconstructed nipple through the medication opening.

7. The method of claim 6 wherein said attaching includes securing the free end portion of a tape, which tape is secured at another end thereof to the pad, to the patient's breast.

8. A surgical wound protector for a raised wound on a patient comprising:
    a sterile pad having an upper surface, a lower surface, and a centrally-located pad opening therethrough passing through said upper and lower surfaces,
    a cone-shaped raised wound protector member having a base portion, said base portion defining a base portion opening, and an upper dome portion connected above said base portion and having the interior thereof configured to receive the patient's raised wound thereinto up through said base portion opening when said lower surface is placed against the patient around the raised wound,
    a securing means for securing said protector member to said sterile pad so that said base portion opening is positioned over said pad opening,
    an adhesive securing means for securing said sterile pad to the patient so that the raised wound passes up through said pad opening and into said protector member,
    said dome portion having a top end portion and a raised annular rim thereabout, and
    said raised annular rim defining a plurality of suture holes spaced and positioned so that suture thread can pass therethrough to engage the raised wound and hold it in position in and relative to said protector member.

9. The wound protector of claim 8 wherein said protector member defines an access opening providing access to suture thread in the interior of said protector member to assist in a suturing procedure through said suture holes.

10. The wound protector of claim 9 wherein said access opening passes through said top end portion.

11. The wound protector of claim 8 wherein said protector member is formed of a clear plastic material.

12. The wound protector of claim 8 wherein said plurality of spaced suture holes comprise at least three spaced holes on a circle defined by said annular rim.

13. The wound protector of claim 8 wherein said protector member has an outwardly-disposed flange at said base portion, and said securing means secures said flange to said upper surface.

14. The wound protector of claim 8 wherein said suture holes are positioned on a circle about a longitudinal axis of said protector member.

15. The wound protector of claim 8 wherein said protector member has its longitudinal axis defining the center of said annular rim.

16. The wound protector of claim 8 wherein said securing means comprises a circular tape portion about said protector member and attaching said protector member to said pad, and said adhesive securing means comprises a plurality of tape strips disposed radially out from said pad.

17. The wound protector of claim 16 wherein said circular tape portion and said tape strips define a continuous tape member.

18. The wound protector of claim 16 wherein said protector member has an annular flange at said base portion, and said circular tape portion directly engages said annular flange.

19. The wound protector of claim 8 wherein said raised wound is a reconstructed nipple of the patient, and said protector member is configured to receive the reconstructed nipple thereinto so that said protector member is positionable spaced about and over the reconstructed nipple.

20. The wound protector of claim 8 wherein said top end portion is generally flat.

21. The wound protector of claim 8 wherein said protector member defines a medication opening therethrough, within said annular rim, and through which medication can be applied to the raised wound when said adhesive securing means is securing said protector member to the patient over the raised wound.

22. The wound protector of claim 21 wherein said medication opening directly engages the inner surface of said annular rim.

23. A surgical wound protector comprising:
   a sterile pad having an upper surface, a lower surface, and a centrally-located opening therethrough engaging said upper and lower surfaces,
   a cone-shaped protector member formed of tissue-compatible, generally transparent plastic, and having a base portion and a top portion,
   said protector member having at said base portion a radially-disposed flange with an upper annular flange surface,
   a securing means for securing said base portion to said sterile pad upper surface and over said centrally-located opening, and for securing said sterile pad to a patient so that said protector encompasses a raised projection on the patient which passes up through said opening and into said projector member,
   said securing means directly securing said flange to said upper surface to said pad,
   said securing means including a continuous tape member engaging said upper annular flange surface and a plurality of tape strips radially disposed out from said pad, and
   said top portion defining at least one air hole passing therethrough for aerating the patient's raised projection positioned in said protector member.

24. The wound protector of claim 23 wherein said air hole has a diameter of 0.062 inch.

25. The wound protector of claim 23 wherein said at least one air hole comprises four spaced air holes.

26. The wound protector of claim 23 wherein said top portion is smooth and rounded and forms a downwardly-disposed dome.

27. The wound protector of claim 23 wherein said plurality of tape strips comprises four tape strips spaced ninety degrees relative to each other.

28. The wound protector of claim 23 wherein said continuous tape member comprises an inner circular tape portion having a central opening through which said nipple protector member passes and said tape strips extend radially out from said inner circular tape portion.

29. The wound protector of claim 28 wherein the outer diameter of said inner circular tape portion is less than the outer diameter of said pad.

30. The wound protector of claim 23 further comprising removable protective paper on the inner surface of said tape strips.

31. The wound protector of claim 23 further comprising a sterile package enclosing said sterile pad, said protector member, and said securing means.

32. The wound protector of claim 23 wherein said protector member is sized and shaped to protect an areola/nipple area of the patient.

33. The wound protector of claim 23 wherein said protector member is sized and shaped to protect a reconstructed nipple of the patient.

34. The wound protector of claim 23 wherein said protector member is sized and shaped to protect a raised boil of the patient.

35. The wound protector of claim 23 wherein said protector member is sized and shaped to protect an umbilical cord of the patient.

36. The wound protector of claim 23 wherein said protector member is sized and shaped to protect a support for a trachea or a drainage tube of the patient.

* * * * *